United States Patent
Desai et al.

(10) Patent No.: US 12,318,067 B2
(45) Date of Patent: Jun. 3, 2025

(54) STEERABLE AND FLEXIBLE ROBOTIC ENDOSCOPIC TOOLS FOR MINIMALLY INVASIVE PROCEDURES

(71) Applicant: Georgia Tech Research Corporation, Atlanta, GA (US)

(72) Inventors: Jaydev P. Desai, Atlanta, GA (US); Yash Chetan Chitalia, Atlanta, GA (US); Seokhwan Jeong, Atlanta, GA (US); Joshua J. Chern, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 742 days.

(21) Appl. No.: 17/433,165

(22) PCT Filed: Mar. 4, 2020

(86) PCT No.: PCT/US2020/020942
§ 371 (c)(1),
(2) Date: Aug. 23, 2021

(87) PCT Pub. No.: WO2020/180957
PCT Pub. Date: Sep. 10, 2020

(65) Prior Publication Data
US 2022/0151473 A1    May 19, 2022

Related U.S. Application Data

(60) Provisional application No. 62/813,444, filed on Mar. 4, 2019.

(51) Int. Cl.
*A61B 1/00* (2006.01)
*A61B 1/005* (2006.01)
(Continued)

(52) U.S. Cl.
CPC .......... *A61B 1/00087* (2013.01); *A61B 1/005* (2013.01); *A61B 1/0125* (2013.01); *A61B 1/018* (2013.01)

(58) Field of Classification Search
CPC ........ A61B 1/005; A61B 1/0125; A61B 1/018
See application file for complete search history.

(56) References Cited

U.S. PATENT DOCUMENTS 6,012,494 A    1/2000   Balazs
6,749,560 B1 *  6/2004   Konstorum ........ A61B 1/00071
                                                    604/525

(Continued)

FOREIGN PATENT DOCUMENTS

DE    10 2009 037 030 A1    2/2011
JP    2014-000265 A         1/2014

(Continued)

OTHER PUBLICATIONS

Office Action from Japanese Application No. 2021-553091 dated Feb. 6, 2020 (with Machine Transcription).

(Continued)

*Primary Examiner* — Dung T Ulsh
(74) *Attorney, Agent, or Firm* — Troutman Pepper Locke LLP; Ryan A. Schneider; Korbin M. Blunck

(57) ABSTRACT

A probe part (100) includes a base member (110) defining a first bore (112). A first elongated elastic member (120) includes a near end (126) secured to the base member (110) and extends therefrom to a far end (128) and defines a channel (125) in communication with the first bore (112) and that runs lengthwise with the first elongated elastic member (120). A first tendon (130) has a first end and an opposite second end that is secured to the first elongated elastic member (120) adjacent to the far end (128). The first tendon (130) runs through the channel (125) adjacent the first side (122) and exits through the first bore (112) exiting outwardly (Continued)

therefrom. Applying tension to the first tendon (130) causes the first elongated elastic member (120) to bend in the direction of the first side (122).

18 Claims, 8 Drawing Sheets

(51) Int. Cl.
*A61B 1/012* (2006.01)
*A61B 1/018* (2006.01)

(56) References Cited

U.S. PATENT DOCUMENTS

| | | |
|---|---|---|
| 10,321,804 B2 * | 6/2019 | Jacobsen ............... A61B 1/05 |
| 10,617,438 B2 | 4/2020 | O'Keefe et al. |
| 2001/0037084 A1 * | 11/2001 | Nardeo ............ A61M 25/0141 |
| | | 604/95.04 |
| 2005/0096694 A1 | 5/2005 | Lee |
| 2007/0021737 A1 | 1/2007 | Lee |
| 2007/0225562 A1 * | 9/2007 | Spivey ................ A61B 1/0057 |
| | | 600/121 |
| 2009/0062606 A1 * | 3/2009 | Ueda .................. A61B 1/00078 |
| | | 600/114 |
| 2012/0053415 A1 * | 3/2012 | Bunch ............... A61M 25/0136 |
| | | 600/121 |
| 2017/0065153 A1 | 3/2017 | Fujitani |
| 2018/0228346 A1 | 8/2018 | Sekowski |
| 2020/0221927 A1 * | 7/2020 | Matthison-Hansen ...................... |
| | | A61B 1/012 |
| 2020/0268238 A1 * | 8/2020 | Jensen ............... A61B 1/00165 |
| 2020/0281666 A1 * | 9/2020 | Gunn ..................... A61B 34/30 |

FOREIGN PATENT DOCUMENTS

| | | |
|---|---|---|
| JP | 2014090800 A | 5/2014 |
| JP | 2018-534052 A | 11/2018 |
| WO | 2017/213491 A1 | 12/2017 |

OTHER PUBLICATIONS

European Patent Office: "Supplementary European Search Report"; Sep. 30, 2022 (Search Report in corresponding European Application No. EP 20 76 6820).

* cited by examiner

STEERABLE AND FLEXIBLE ROBOTIC ENDOSCOPIC TOOLS FOR MINIMALLY INVASIVE PROCEDURES

CROSS-REFERENCE TO RELATED APPLICATION(S)

This application claims the benefit of U.S. Provisional Patent Application Ser. No. 62/813,444, filed Mar. 4, 2019, the entirety of which is hereby incorporated herein by reference.

BACKGROUND OF THE INVENTION

1. Field of the Invention

The present invention relates to endoscopic tools and, more specifically, to a steerable probe part.

2. Description of the Related Art

Hydrocephalus is a common pediatric disease occurring at a rate of about 0.7 cases per thousand in most developed countries. This number is even higher in developing countries. This condition occurs due to a buildup of cerebrospinal fluid (CSF) in the brain leading to the enlargement of the ventricles and intracranial pressure increase. CSF is believed to be produced in the lateral ventricles, passing successively through the third ventricle, cerebral aqueduct, fourth ventricle prior to its exit into the cisternal spaces around the cranio-cervical junction. One of the most common causes of hydrocephalus is due to blockage of CSF circulation at the level of the cerebral aqueduct, which connects the third and fourth ventricles. Delay in the treatment of hydrocephalus can result in the loss of motor function, epilepsy, chronic headaches, sensory damage and death. Most commonly, clinicians would treat hydrocephalus by diverting the CSF through implantation of a silicone tubing between the brain and the abdomen (CSF shunts). However, six decades worth of experiences with CSF shunts have shown that they are imperfect devices, with the blockage of shunts being the number one cause of morbidity and mortality.

An alternative to CSF shunt placement were brain endoscopic procedures with the purpose of removing the blockage or bypassing the blockage within the brain, thus avoiding implantation of a CSF shunt altogether. One of the most common brain endoscopic procedures is the endoscopic third ventriculostomy (ETV). During ETV, the surgeon first makes an entry into the ventricle using an endoscope, composed of a high definition camera and a light source. Under direct visualization, the surgeon then makes a perforation on the floor bottom wall of the third ventricle using a rigid instrument passed through the working channel of the endoscope. This perforation allows the CSF to bypass the blockage at the cerebral aqueduct and to egress into the prepontine cisterns located under the third ventricle. While this procedure has seen a success rate of over 80% in infants, reaching a suitable location in the third ventricle for penetration in an ETV procedure can be difficult. Because of the rigid nature of the endoscope, a linear pathway from the scalp, through the brain parenchyma, down to the level of the third ventricular floor is required. This linear pathway must avoid traversing important blood vessels, functional areas and cranial nerves to avoid hemorrhaging. Further complicating the issue is the fact that the brain anatomy is often distorted due to the disease process. Because of all these restrictions, finding an optimal linear pathway may not always be possible.

Therefore, there is a need for steerable endoscopic probe assembly that can avoid obstacles.

SUMMARY OF THE INVENTION

The disadvantages of the prior art are overcome by the present invention which, in one aspect, is a probe part that includes a base member defining a first bore passing therethrough. A first elongated elastic member has a first side and an opposite second side, the first elongated elastic member includes a near end secured to the base member and extends therefrom to a far end. The first elongated elastic member defines a first channel that is in communication with the first bore and that runs lengthwise along the first elongated elastic member. A first tendon, a portion of which is disposed in the first channel adjacent to the first side of the first elongated elastic member, has a first end and an opposite second end. The second end is secured to the first elongated elastic member adjacent to the far end. The first tendon exits through the first bore so that the first end extends outwardly therefrom. Applying tension to the first tendon causes the first elongated elastic member to bend in the direction of the first side of the first elongated elastic member.

In another aspect, the invention is a probe assembly that includes a base member defining a first bore, a second bore, a third bore and a fourth bore passing therethrough. A first elongated elastic member has a first side and an opposite second side. The first elongated elastic member including a near end secured to the base member and extending therefrom to a far end. The first elongated elastic member defines a first passage aligned with the first bore and running lengthwise adjacent to the first side of the first elongated elastic member. The first elongated elastic member also defining a second passage aligned with the second bore and running lengthwise adjacent to the second side of the first elongated elastic member. An intermediate rigid member is affixed to the far end of the first elongated elastic member. A second elongated elastic member is affixed to the intermediate rigid member opposite from the first elongated elastic member. The second elongated elastic member has a first side and an opposite second side. The second elongated elastic member defines a third passage running lengthwise adjacent to the first side of the second elongated elastic member. The second elongated elastic member also defines a fourth passage running lengthwise adjacent to the second side of the first elongated elastic member. A first tendon has a first end and an opposite second end. The second end is secured to the first elongated elastic member adjacent to the far end. The first tendon runs through the first passage and exits through the first bore so that the first end extends outwardly therefrom. Applying tension to the first tendon causes the first elongated elastic member to bend in the direction of the first side of the first elongated elastic member. A second tendon has a first end and an opposite second end. The second end is secured to the first elongated elastic member adjacent to the far end. The second tendon runs through the second passage and exits through the second bore so that the first end extends outwardly therefrom. Applying tension to the second tendon causes the first elongated elastic member to bend in the direction of the second side. A third tendon has a first end and an opposite second end. The second end is secured to the second elongated elastic member adjacent to the far end. The third tendon runs through the third passage defined by the second elongated elastic member, through a third passage defined by the first elongated elastic member and exits through a third bore in the base member so that the first end extends outwardly therefrom. Applying tension to the third tendon causes the second elongated elastic member to bend in the direction of the first side of the second elongated elastic member. A fourth tendon has a first end and an opposite second end. The second end is secured to the second elongated elastic member adjacent to the far end. The fourth tendon runs through the fourth passage and exits through a fourth bore in the base member so that the first end extends outwardly therefrom. Applying tension to the fourth tendon causes the second elongated elastic member to bend in the direction of the second side of the second elongated elastic member.

In yet another aspect, the invention is a tool for operating a probe assembly that includes at least one elastic member having directional control as a result of applying stress to at least one tendon. The tool is configured to be used with an endoscope that defines a lengthwise passage passing therethrough. A housing has an interior that is configured to be accessed by retracting a retractable portion. The housing has an end that is configured for joining with an endoscope. At least one input passage is defined by the housing and is configured to be aligned with the lengthwise of the endoscope. The at least one input passage is configured to receive a portion of the at least one tendon therein so that the at least one elastic member is received into the lengthwise passage defined by the endoscope. An actuator assembly is affixed to the housing and is configured to manipulate the at least one tendon by selectively applying stress thereto.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
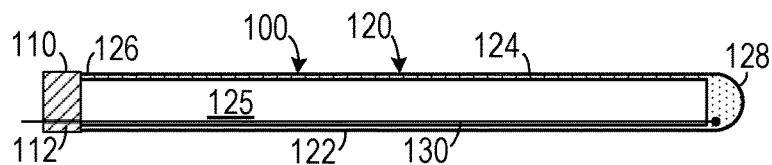
FIGS. 1A and 1B are schematic diagrams of one representative embodiment of a probe part.

A preferred embodiment of the invention is now described in detail. Referring to the drawings, like numbers indicate like parts throughout the views. Unless otherwise specifically indicated in the disclosure that follows, the drawings are not necessarily drawn to scale. The present disclosure should in no way be limited to the exemplary implementations and techniques illustrated in the drawings and described below. As used in the description herein and throughout the claims, the following terms take the meanings explicitly associated herein, unless the context clearly dictates otherwise: the meaning of "a," "an," and "the" includes plural reference, the meaning of "in" includes "in" and "on."

A robotically-operable steerable probe assembly of the present invention is designed to fit in the small diameters of the working channels in commonly used endoscopes (such as the MINOP endoscope available from Acsculap Inc., which has a 2.2 mm working channel or the HandyPro endoscope available from Karl Storz SE & Co. KG with a 1.3 mm working channel). It is also designed to be highly maneuverable in its workspace, so that it can have a higher chance of avoiding obstacles. Also, in the operating room, it is often desirable to have two surgeons participating in endoscopic surgeries, where one surgeon directs the endoscope, inserting and retracting the scope body, while the other surgeon operates the instrument itself, including the insertion, retraction and rotation of the tool in the working channel of the endoscope. As a result, a robotic solution should include an actuator that can be operated in a small hand-held package.

The robotic probe system of the present invention includes three major components: 1) a compliant elongated elastic member proximal joint that is highly resistive to transverse forces, 2) a tendon phase shifting unit, that allows the distal tendons to be rerouted such that inter-joint coupling is minimized, and 3) a highly compliant elongated elastic member distal joint.

Figure 1B:
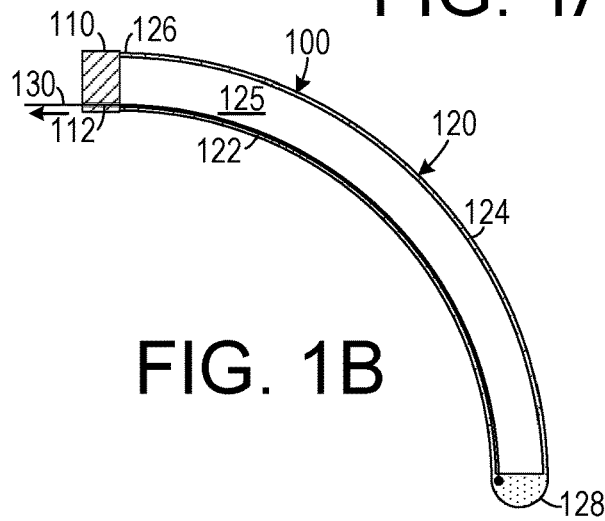

As shown in FIG. 1, one embodiment of a probe part 100 includes a base member 110 that has a first bore 112 passing therethrough. A first elongated elastic member 120 (also referred to herein as a "joint") extends from the base member 110 and has a first side 122, an opposite second side 124 a near end 126 and a far end 128. The first elongated elastic member 120 defines a channel 125 that extends along the first side 122 and that is in alignment with the bore 112. A first tendon 130 runs through the bore 112 and the channel 125 and is secured to the first elongated elastic member 120 near the far end 128. As shown in FIG. 1B, applying stress to the first tendon 130 in the direction shown results in the first elongated elastic member 120 being bent inwardly in the direction of the first side 122.

Figure 2A:
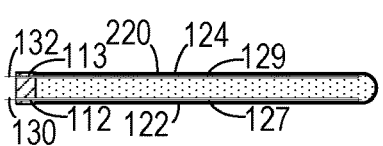
FIGS. 2A-2C are schematic diagrams of a second embodiment of a probe part.
Figure 2B:
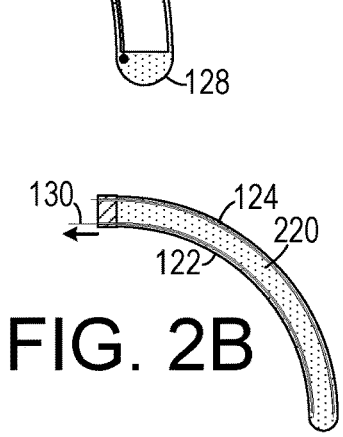
Figure 2C:
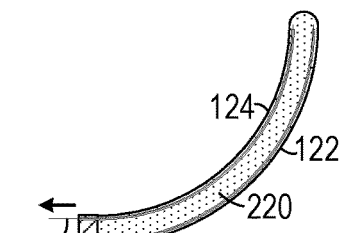

As shown in FIGS. 2A-2C, the first elongated elastic member 220 can also define a first passage 127 and a second passage 129 along the second side and the base member can define a second bore 113 through which a second tendon 132 runs. This embodiment allows the first elongated elastic member 120 to be bent in both the direction of the first side 122 and also in the direction of the second side 124 by pulling on the tendons. In one embodiment, the tendons may include nickel titanium alloy (such as Nitinol) wires (such as part number WSE000450000DG available from https://shop.confluentmedical.com/). It is understood that the tendons may include other materials, including other types of lines, wires, cords, etc., depending upon the specific application, without departing from the scope of the invention.

Figure 3:
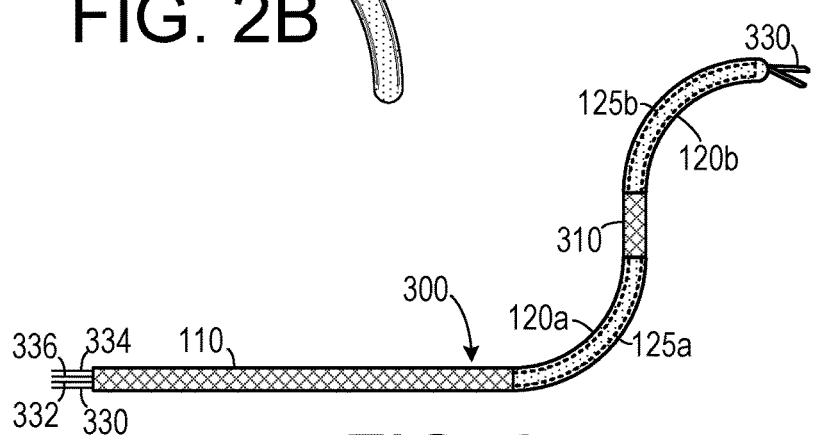
FIG. 3 is a schematic diagram of one embodiment of a probe.

As shown in FIG. 3, a probe assembly 300 can include a first elongated elastic member 120a (controlled by tendons 330 and 332) and a second elongated elastic member 120b (controlled by tendons 334 and 336) that are separated by an intermediate rigid member 310 that is configured as a phase shifting unit. The first elongated elastic member 120a defines channel 125a and the second elongated elastic member defines channel 125b. This probe assembly 300 is able to achieve such configurations as the "S" curve shown. Additionally, a tool 330 may be affixed to the end of the probe assembly 300 (which can also include a passage for a line used to control the tool 330) for use in the application of the probe assembly 300. In certain embodiments, a plurality of elongated elastic members may be coupled in series and separated from each other by a corresponding plurality of intermediate rigid members to achieve more complex movement patterns in the probe assembly. While the elongated elastic members are shown as being substantially tubular, they may taper or vary in diameter along their length depending upon the specific application. In yet another embodiment, the elongated members may have a non-tubular structure, such as a rectangular beam.

Figure 4A:
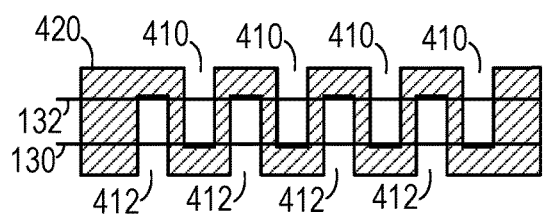
FIGS. 4A-4B are schematic diagrams of a crenulated tube elastic member.
Figure 4B:
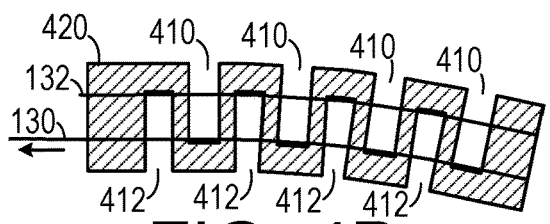

As shown in FIGS. 4A-4B, the elongated elastic members can include an elastic tube 420 into which is machined a first set of crenulations 410 on one side and a second set of crenulations 412 on the other side. In one embodiment, the elastic tube 420 includes nickel titanium alloy. (It is understood that the elastic tube 420 may include other materials that exhibit elastic properties depending upon specific applications without departing from the scope of the invention.) When one of the tendons 130, as shown in FIG. 4B, is pulled outwardly, then the adjacent crenulations 412 are bend so as to be compressed, thereby bending the elongated elastic member in the direction of the side of the tendon 130 to which tension is applied. Once the tension is released, then the elongated elastic member will resume its original shape due to the superelastic property of nickel titanium alloy. However, this motion capability can be observed in other materials as well and is not necessarily limited to nickel titanium alloy. Furthermore, the elastic member may be joined to a non-elastic member through micro-welds for lowering the component costs.

Figure 5A:
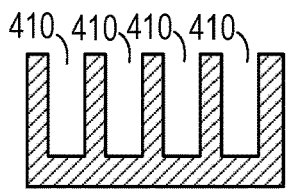
FIGS. 5A-5C are schematic diagrams of different crenulation patterns.
Figure 5B:
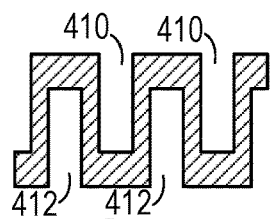
Figure 5C:
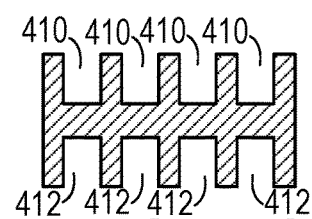
Figure 6:
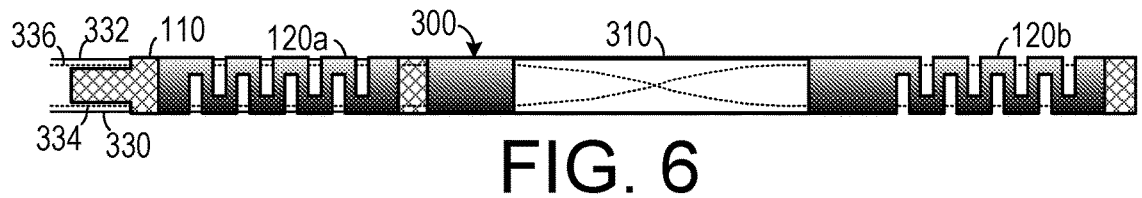
FIG. 6 is a schematic diagram of a probe employing crenulated elastic members.

FIG. 5A, shows a one-sided crenulation pattern, which allows bending in only one direction. FIG. 5B shows an asymmetric crenulation pattern and FIG. 5C shows a symmetric crenulation pattern, both of which allow bending in two directions. A probe assembly 200 employing crenulated elastic members 120 and 220 is shown in FIG. 6 (several other configurations are shown in FIGS. 14A-14D). Returning to FIG. 6, a portion of the inter-joint coupling intermediate member 310 is shown open to demonstrate phase-shifting routing of tendons 334 and 336.

Figure 7A:
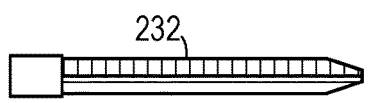
FIGS. 7A-7C are schematic diagrams of tools for use with probes.
Figure 7B:
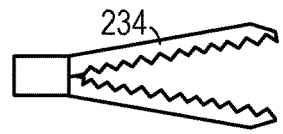
Figure 7C:
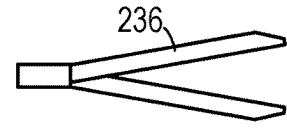

Different tools are shown in FIGS. 7A-7C, which can include a bipolar electro-cautery tool 232, a gripping tool 234 and a scissor tool 236. It should be understood that other types of tools could also be employed, including, for example, an ablation tool, a basket tool, a loop tool, a knife tool, etc.

Figure 8:
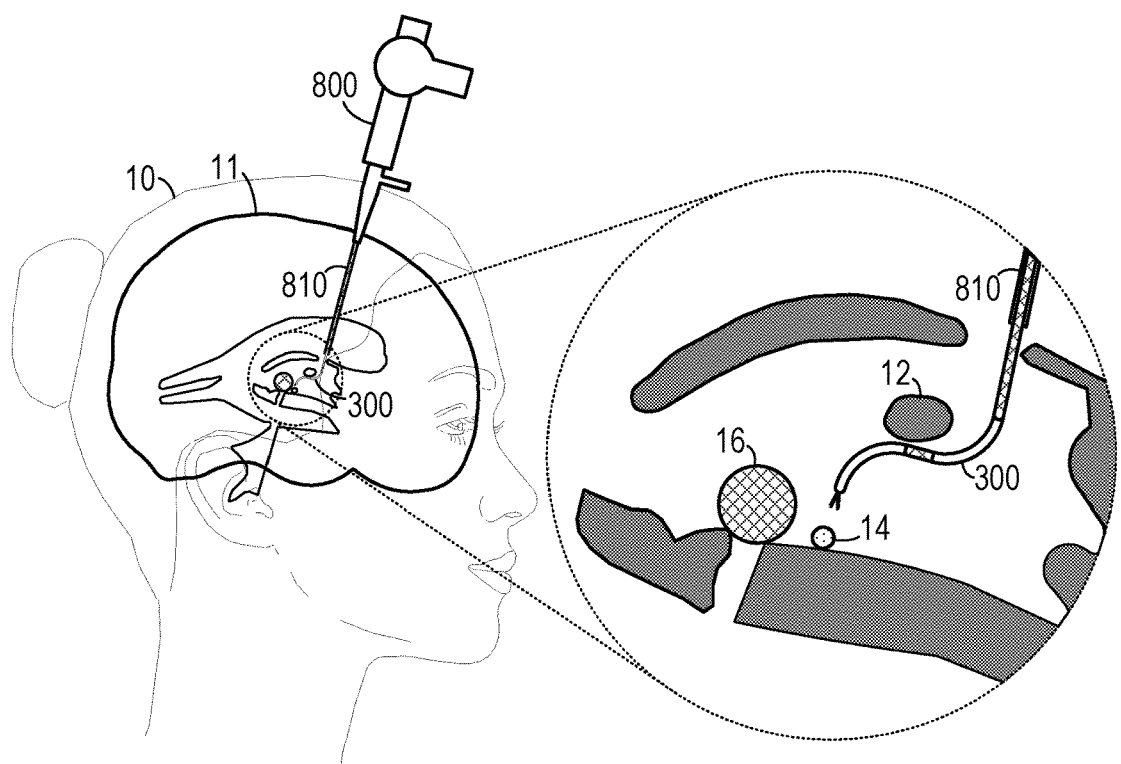
FIG. 8 is a schematic diagram that demonstrates use of a probe with an endoscope.

One embodiment of a probe assembly 300 being employed with a rigid endoscope 810 to perform an operation on the brain 11 of a patient 10 is shown in FIG. 8. This embodiment also shows an actuator assembly 800 used to control the probe assembly 300. As can be seen in the detail, the probe assembly 300 can be manipulated about obstructions 12 to reach a target area 14 for further manipulation to, for example, avoid a tumor 16.

Figure 9:
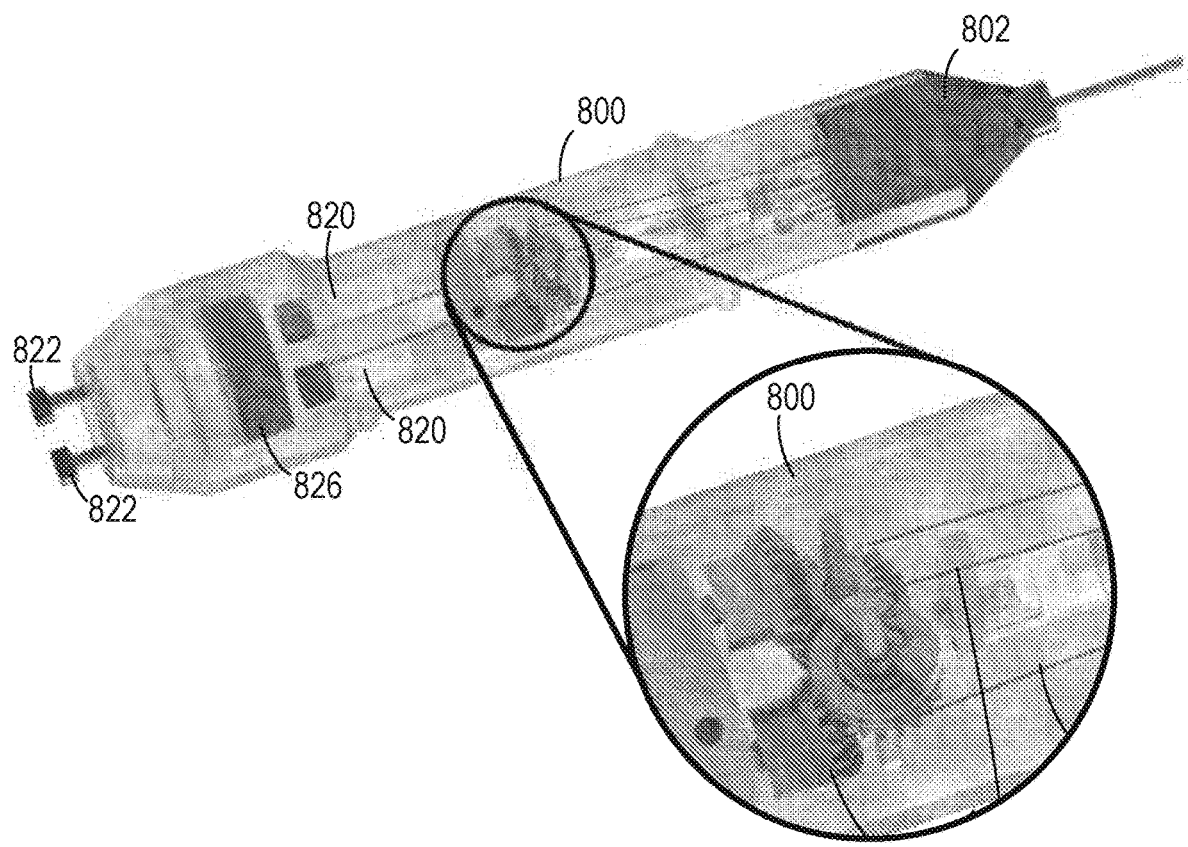
FIG. 9 is a schematic diagram of a probe controlling housing.
Figure 10:
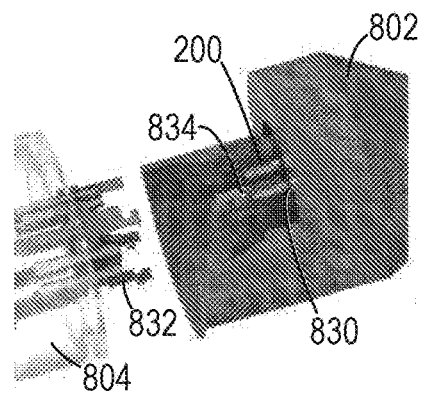
FIG. 10 is a detail of the housing shown in FIG. 9, showing probe connections.
Figure 11:
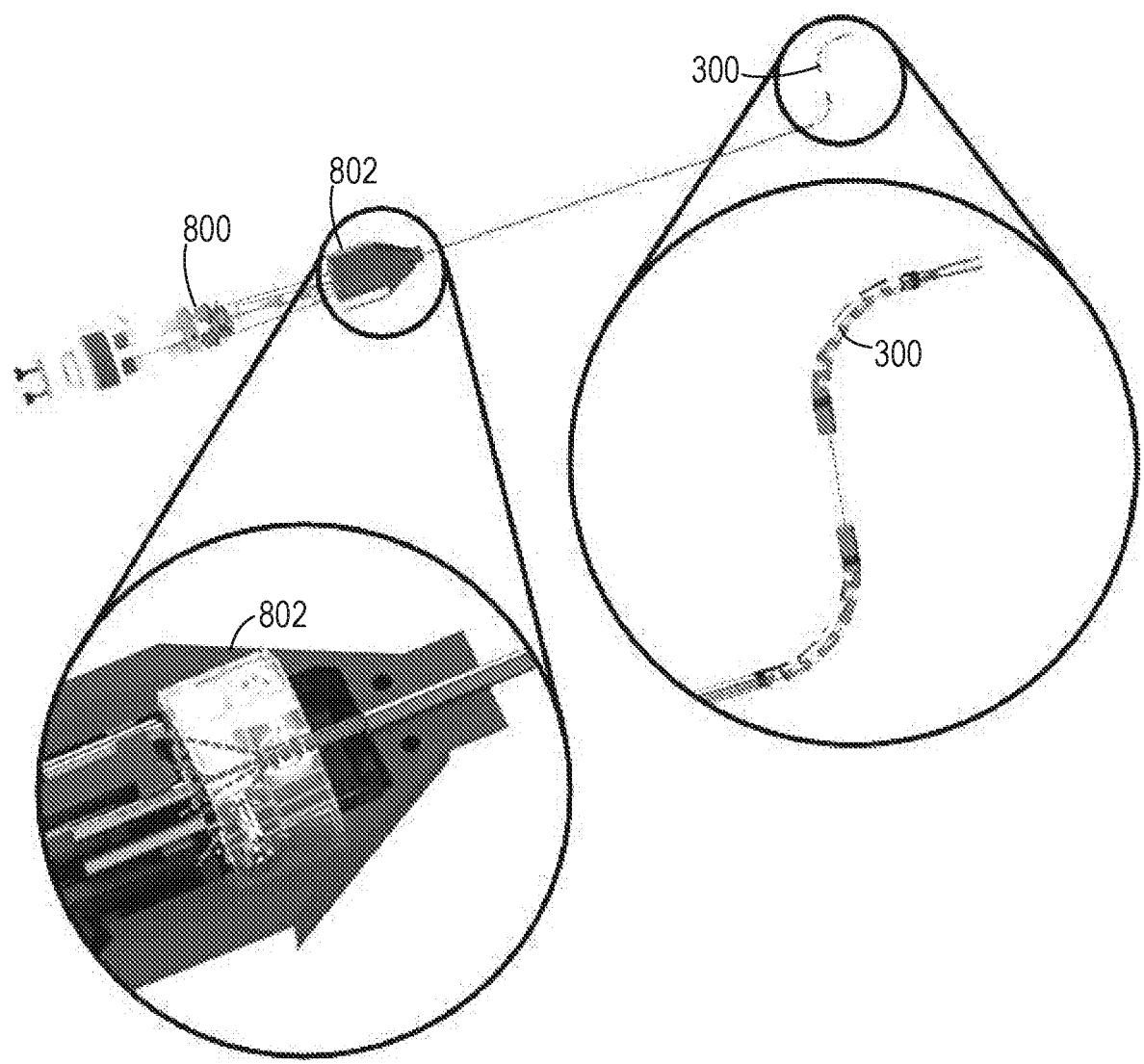
FIG. 11 is a detail of a probe coupled to a housing.
Figure 12:
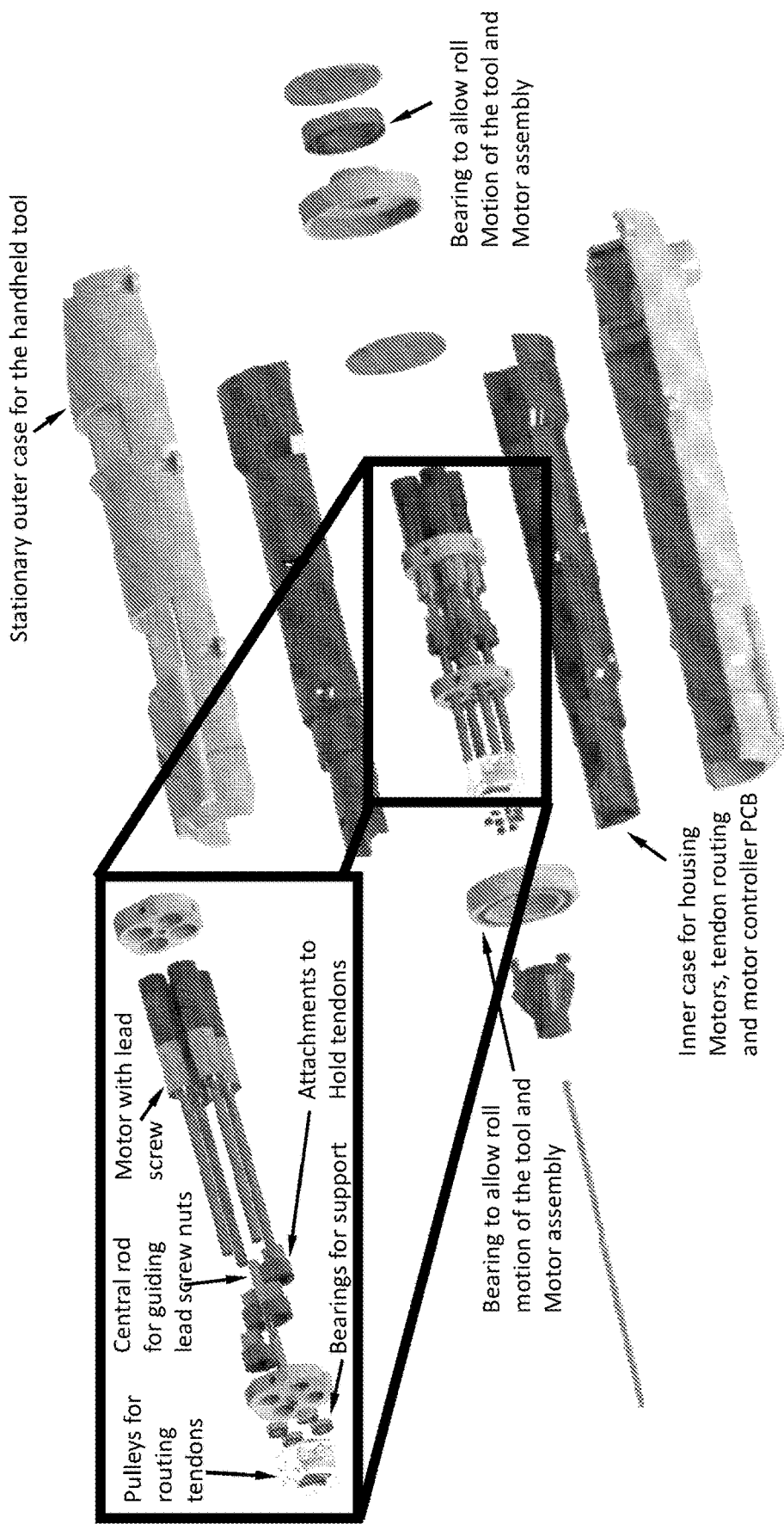
FIG. 12 is an exploded simulated drawing of a controller.
Figure 13:
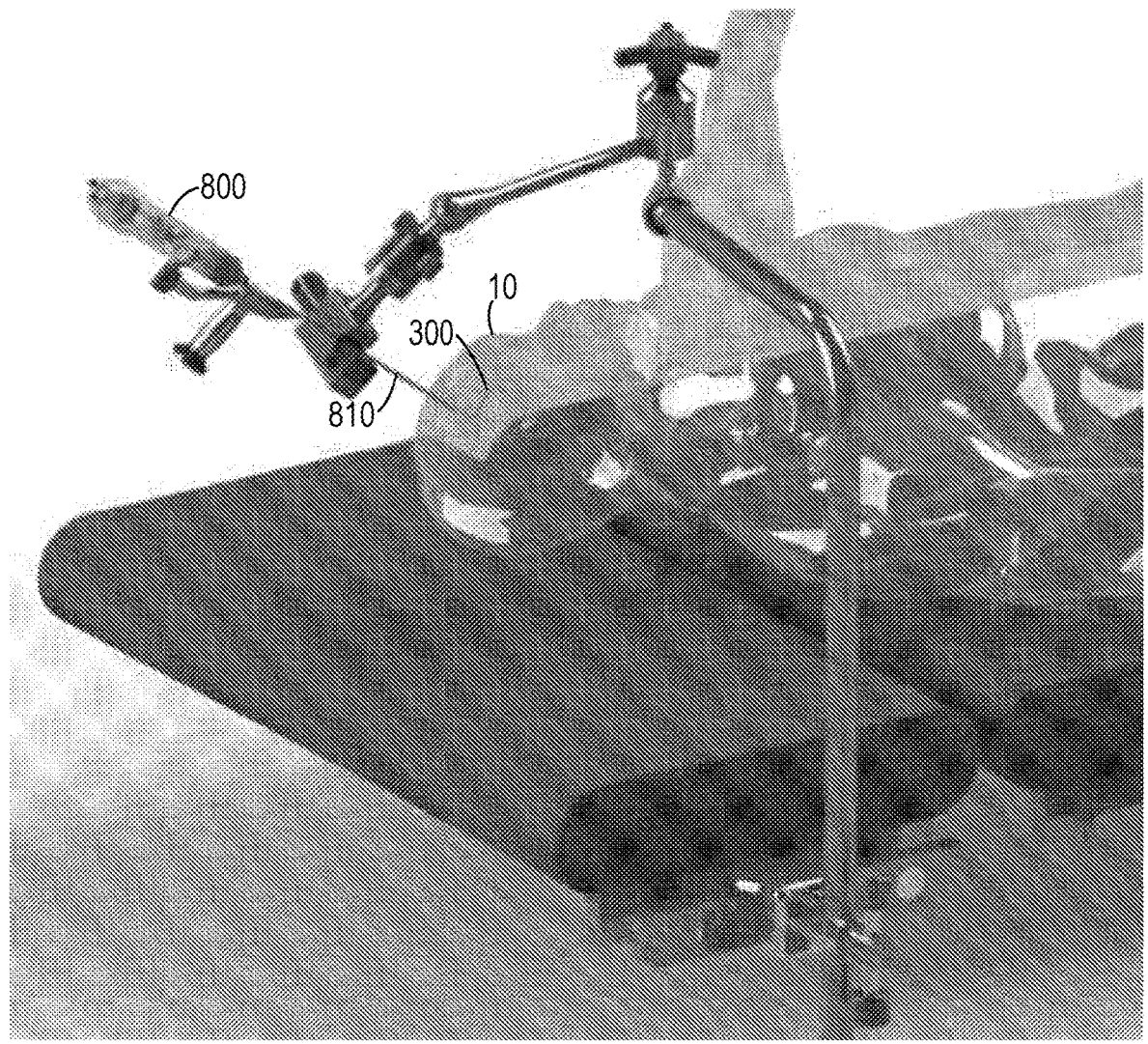
FIG. 13 is a simulated drawing demonstrating use of a probe and a housing being used with an endoscope.
Figure 14A:
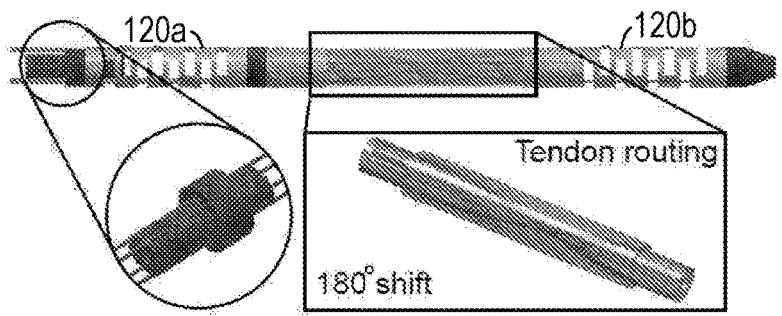
FIGS. 14A-14D are simulation drawings that show several different designs for a probe assembly.
Figure 14B:
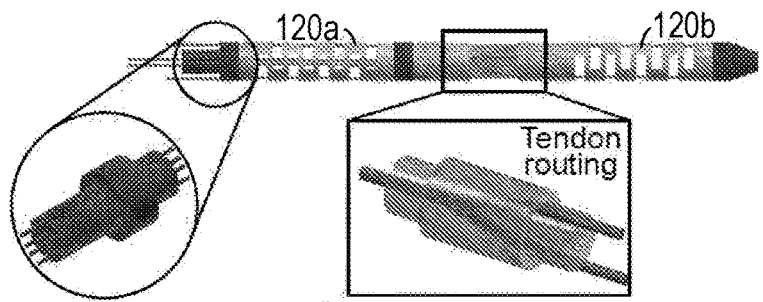
Figure 14C:
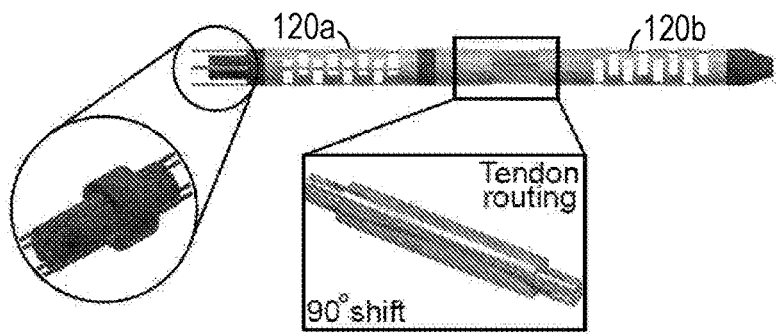
Figure 14D:
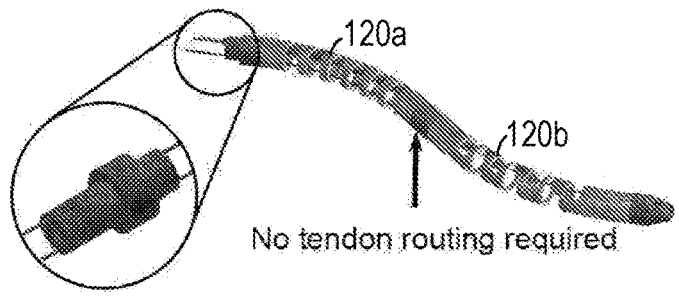

The controller 800, as shown in FIG. 9, can employ two motors (or more) 820 that drive a gear assembly 824 that is used to apply tension to (and release tension from) the tendons. User operated joysticks 822 control movement of the motor 820. A circuit 826 is used to convey control commands from the joysticks 822 and a remote computer to the motors 820. This provides the user with intuitive control of the probe assembly. A quick connect assembly 802, as shown in FIG. 10, includes a retractable housing portion 804 that exposes input passages 830 into which the tendons (130, 132, 134 and 136) of the probe assembly 300 may be placed. (One embodiment includes two or more passages that would allow two or more probe assemblies to be placed therein, thereby allowing two or more tools to be passed through the endoscope.) Probe-side tendon connectors 834 engage actuator-side tendon connectors 832, which are manipulated by the pulley and gear assembly 824. The quick connect assembly 802 may be snapped in place with an insertion and twisting motion in one embodiment. In another embodiment, the snapping and connection may occur magnetically. This quick connect assembly 802 allows for probes with different tools to be removed and preplaced within the endoscope during an operation. The controller 800 for operating the robotic tool tip should be in the range of existing devices used with commercially available endoscopes in terms of its size. Thus, in the experimental embodiment, the controller module has a diameter of 32 mm and length 178.85 mm, making it comparable to the size of existing products. This embodiment of the controller is easily able to dock itself into a connector module that interfaces with the MINOP neuroendoscope. This connector has a female socket that slides onto the neuroendoscope allowing for fine control of the tool tip position and the capability to be secured to the scope by a set screw for hands-free operation. The outer sheath of the controller also has a window for a clinician to be able to roll the entire motor and robot assembly along its central axis, to achieve yet another degree-of-freedom that is already available in existing devices. An exploded view of yet another embodiment of the controller is shown in FIG. 12. All of the joints for the designs are tendon driven. All tendons are controlled by prismatic actuation achieved by DC motors with lead screws. Individual joint tendons are routed via a pulley arrangement to a single DC motor, thereby employing two motors per joint. For designs using 2-4 tendons, the controller allows room for up to four DC Motors of diameter 8 mm (Maxon Precision Motors, MA, United States) with lead screws of length 50 mm and pitch 0.5 mm. All four lead screws are mounted with nuts that hold the tendons which are resting on a single central rod. This rod prevents the nuts from rotating, thereby causing them to slide along the length of this rod achieving prismatic motion. This entire motor and lead screw assembly is resting on two bearings at either end of the controller and is placed in an inner housing. These bearings therefore allow the housing to be rotated along the central axis of the entire cylindrical assembly allowing for the previously described rolling motion. A probe system of this type is shown in FIG. 11. This system in use during an operation is shown in FIG. 13.

Figure 15:
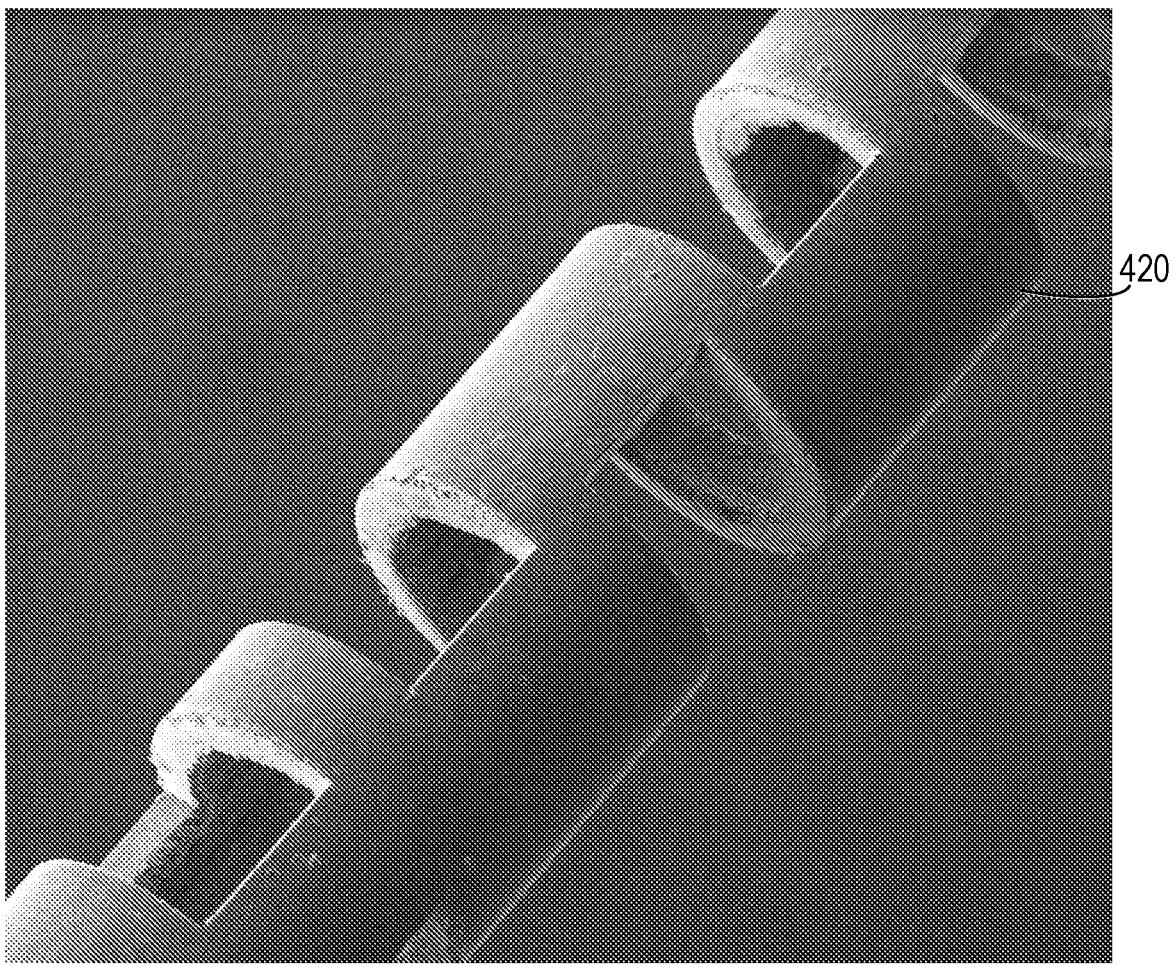
FIG. 15 is a micrograph of a crenulated nickel titanium alloy tube.

In one experimental embodiment, due to the size constraint on the robot diameter, bending flexural joints (elongated elastic members) were made by machining away material from a tube form a specific pattern. In one embodiment, unidirectional asymmetric notch joints were made by removing material from a tube in an asymmetric manner. However, it was found that when all notches lie on one side of the central axis of the tube resulted in the pushing of the neutral axis of the joint to the far end. This made the joint susceptible to transverse forces and other external forces. Bi-directional symmetric joints did not give rise to this issue, but they demonstrated a lack a high degree of compliance due to their limited moment arm. To keep compliance in the bending plane high, while keeping external forces low, a flexural joint known as the bi-directional asymmetric notch joint was adopted, as shown in FIG. 15. In this design, asymmetric notches were created on both sides of the central axis, to create a compliant bending segment between the notch. This type of a joint is capable of withstanding high axial forces as well as forces in the plane transverse to the bending plane. This ability of the notch joint to resist transverse forces allows a tendon routing strategy that minimizes inter-joint coupling.

Figure 16:
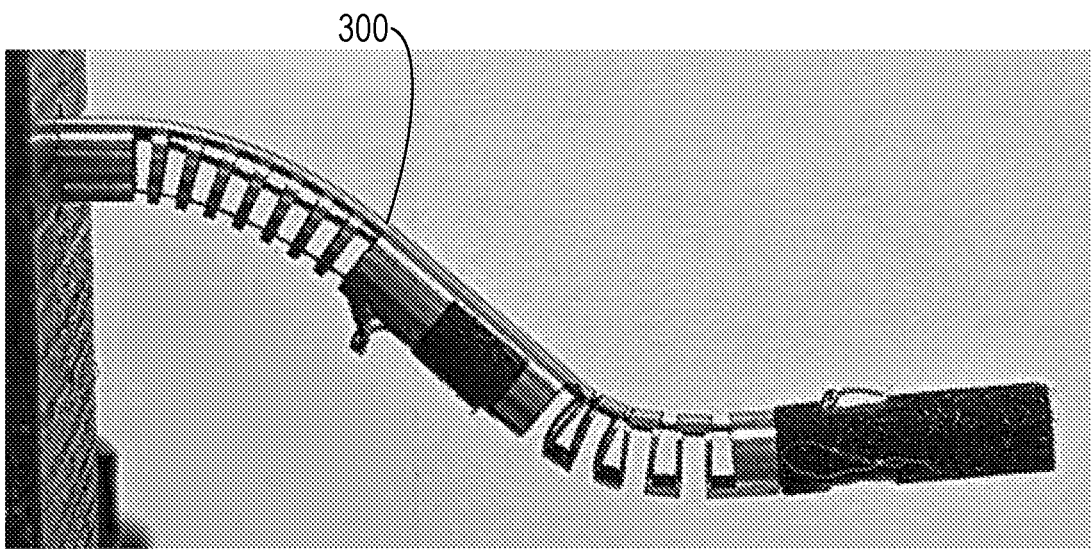
FIG. 16 is a photograph of an experimental embodiment of a probe assembly.

To manufacture the joints used in the experimental embodiment, nickel titanium alloy tubes of outer diameter (OD) of 2 mm and inner diameter (ID) of 1.43 mm (available from Confluent Medical, CA, United States) were machined on a 3-axis CNC milling machine (available from Okuma Millac, Okuma America Corporation, NC, United States) with a 500 micron diameter 4 flute end mill (available from Richards Micro Tool 875-TJ-0.020, Mass., United States). The nominal cutting speed was 19 m/min. and the feed rate was 4.2 mm/sec. In another embodiment of the robot, the joints of the robot were manufactured from nickel titanium alloy tubes of 1.93 mm in outer diameter (OD) and 1.49 mm in inner diameter. Micromachining of the crenulations was performed on a femtosecond laser (WS-Flex Ultra-Short Pulse Laser Workstation, available from Optec, Frameries, Belgium). The robotic probe assembly itself included two joints, both bending in the same plane along parallel axes, and both tendon-driven. Each joint could be deflected in each direction in its bending plane by two tendons. However, the two tendons that drive the distal joint were routed along with the tendons driving the proximal joint. The distal joint tendons were routed on a plane transverse to the bending plane of the proximal joint. Since the proximal joint was designed to have high compliance in its bending plane but low compliance in its transverse plane, actuating the distal tendons did not cause significant deflection of the proximal joint, thus achieving decoupling by design. The tendon phase shifter block was a 3D printed tube with 0.2 mm channels spiraling inside it to allow the distal tendons to shift in phase (by 90°) so that that they could move from the transverse plane to the bending plane of the distal joint. This resulted in a tendon-driven multi-degree of freedom (DoF) system that achieved decoupling by the usage of directionally compliant spring-like joints, and a tendon routing scheme between consecutive joints, as shown in FIG. 16.

Although specific advantages have been enumerated above, various embodiments may include some, none, or all of the enumerated advantages. Other technical advantages may become readily apparent to one of ordinary skill in the art after review of the following figures and description. It is understood that, although exemplary embodiments are illustrated in the figures and described below, the principles of the present disclosure may be implemented using any number of techniques, whether currently known or not.

Modifications, additions, or omissions may be made to the systems, apparatuses, and methods described herein without departing from the scope of the invention. The components of the systems and apparatuses may be integrated or separated. The operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. It is intended that the claims and claim elements recited below do not invoke 35 U.S.C. § 112(f) unless the words "means for" or "step for" are explicitly used in the particular claim. The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A probe part configured to pass through a proximal end of an endoscope, though a working channel of the endoscope, and beyond a distal end of the endoscope, the probe part having a proximal end and a distal end, the probe part configured to locate the distal end of the probe part to a destination location beyond the distal end of the endoscope, the probe part comprising:
   a base member defining a first bore and a spaced apart second bore passing therethrough;
   a first elongated elastic member:
      having a first side and an opposite second side;
      including a near end secured to the base member and extending therefrom to a far end; and
      defining a first channel in communication with the first bore running lengthwise along the first elongated elastic member;
   a second elongated elastic member:
      having a first side and an opposite second side;
      including a near end and extending to an opposite far end;
      defining a second channel in communication with the first channel running lengthwise along the second elongated elastic member;
   an inter-joint coupling intermediate member that:
      couples the second elongated elastic member to the first elongated elastic member; and
      provides an intermediate portion channel between the first and second channels;
   a first tendon having a first end located outside the base member, the first tendon having a portion which is disposed through the first bore which is adjacent to the first side of the first elongated elastic member, and the first tendon having a portion extending to an opposite second end located within the first channel of the first elongated elastic member, the second end of the first tendon being secured to the first elongated elastic member adjacent to the far end, the first tendon exiting through the first bore so that the first end extends outwardly therefrom, such that applying tension to the first tendon causes the first elongated elastic member to bend in the direction of the first side of the first elongated elastic member; and a second tendon having a first end located outside the base member, the second tendon having a portion which is disposed through the second bore which is adjacent to the second side of the first elongated elastic member, and the second tendon having a portion extending to an opposite second end located within the first channel of the first elongated elastic member, the second end of the second tendon being secured to the first elongated elastic member adjacent to the far end, the second tendon exiting through the second bore so that the first end extends outwardly therefrom, such that applying tension to the second tendon causes the first elongated elastic member to bend in the direction of the second side of the first elongated elastic member.

2. The probe part of claim 1, wherein the probe part has a diameter that is less than a working channel of a rigid endoscope.

3. The probe part of claim 1, wherein the first elongated elastic member comprises a tube including a first plurality of crenulations machined into the first side of the first elongated elastic member.

4. The probe part of claim 3, wherein the tube further includes a second plurality of crenulations machined into the second side of the first elongated elastic member.

5. The probe part of claim 4, wherein the first plurality of crenulations are symmetric with the second plurality of crenulations.

6. The probe part of claim 4, wherein the first plurality of crenulations are asymmetric with the second plurality of crenulations.

7. The probe part of claim 1, wherein a tool affixed to the distal end of the probe part is located to the destination, beyond the distal end of the endoscope.

8. The probe part of claim 1 further comprising:
a third tendon having a first end located outside the base member, the third tendon having a portion which is disposed through a third bore in the base member, which is adjacent to the first side of the second elongated elastic member, and the third tendon having a portion extending to an opposite second end located within the second channel of the second elongated member, the second end of the third tendon secured to the second elongated elastic member adjacent to the far end, the third tendon exiting through the third bore so that the first end extends outwardly therefrom, such that applying tension to the third tendon causes the second elongated elastic member to bend in the direction of the first side of the second elongated elastic member.

9. The probe part of claim 8, wherein the second elongated elastic member comprises a tube including a first plurality of crenulations machined into the first side of the second elongated elastic member.

10. The probe part of claim 8 further comprising:
a fourth tendon having a first end located outside the base member, the fourth tendon having a portion which is disposed through a fourth bore in the base member, which is adjacent to the second side of the second elongated elastic member, and the fourth tendon having a portion extending to an opposite second end located within the second channel of the second elongated member, the second end of the fourth tendon secured to the second elongated elastic member adjacent to the far end, the fourth tendon exiting through the fourth bore so that the first end extends outwardly therefrom, such that applying tension to the fourth tendon causes the second elongated elastic member to bend in the direction of the second side of the second elongated elastic member.

11. The probe part of claim 9, wherein the tube further includes a second plurality of crenulations machined into the second side of the second elongated elastic member.

12. The probe part of claim 11, wherein the first plurality of crenulations is symmetric with the second plurality of crenulations.

13. The probe part of claim 11, wherein the first plurality of crenulations is asymmetric with the second plurality of crenulations.

14. The probe part of claim 8, wherein a tool affixed to the distal end of the probe part is located to the destination, beyond the distal end of the endoscope.

15. The probe part of claim 8, wherein:
at least one of the elongated elastic members comprise a plurality of bi-directional asymmetric crenulations machined into the sides;
the presence of the bidirectional asymmetric crenulations keeps sufficient compliance in the bending plane high, while also keeping external forces low; and
the bidirectional asymmetric crenulations create a compliant bending length of the respective one or both of the elongated elastic members, capable of withstanding high axial forces as well as forces in the plane transverse to the bending plane, which resists transverse forces and allows for the tendon routing strategy to minimize inter joint coupling.

16. The probe part of claim 10, wherein:
at least one of the elongated elastic members comprise a plurality of bi-directional asymmetric crenulations machined into the sides;
the presence of the bidirectional asymmetric crenulations keeps sufficient compliance in the bending plane high, while also keeping external forces low; and
the bidirectional asymmetric crenulations create a compliant bending length of one or both of the elongated elastic members, capable of withstanding high axial forces as well as forces in the plane transverse to the bending plane, which resists transverse forces and allows for the tendon routing strategy to minimize inter joint coupling.

17. The probe part of claim 16, wherein:
the elongated elastic members comprise nickel titanium alloy tubes; and
the bidirectional asymmetric crenulations are micromachined with a femtosecond laser.

18. A probe part configured to pass through a proximal end of an endoscope, though a working channel of the endoscope, and beyond a distal end of the endoscope, the probe part having a proximal end and a distal end, the probe part configured to locate the distal end of an instrument passing through the probe part to a destination location beyond the distal end of the probe part endoscope, the probe part comprising:
a base member defining a first bore and a spaced apart second bore passing therethrough;
a first elongated elastic member having a first side and an opposite second side, the first elongated elastic member including a near end secured to the base member and extending therefrom to a far end, the first elongated elastic member defining a first channel in communication with the first bore, running lengthwise along the first elongated elastic member;
a second elongated elastic member having a first side and an opposite second side, the second elongated elastic member including a near end and extending to opposite far end, the second elongated elastic member defining a second channel in communication with the first channel, running lengthwise along the second elongated elastic member;

an inter-joint coupling intermediate member that couples the second elongated elastic member to the first elongated elastic member and provides an intermediate portion channel between the first and second channels;

a first tendon disposed in the first channel adjacent to the first side of the first elongated elastic member, passing through the inter-joint coupling intermediate member and passing through the second channel adjacent to the second side of the second elongated elastic member; and a second tendon disposed in the first channel adjacent to the second side of the first elongated elastic member, passing through the inter-joint coupling intermediate member and passing through the second channel adjacent to the first side of the second elongated elastic member;

wherein:
the inter-joint coupling intermediate member phase-shifts the first tendon and the second tendon so that applying tension to at least one of the first tendon or the second tendon causes the first elongated elastic member to bend along a first plane and the second elongated elastic member to bend along a second plane that is transverse to the first plane;

at least one of the elongated elastic members comprise a plurality of bi-directional asymmetric crenulations machined into the sides;

the presence of the bidirectional asymmetric crenulations keeps sufficient compliance in the bending plane high, while also keeping external forces low;

the bidirectional asymmetric crenulations create a compliant bending length of one or both of the elongated elastic members, capable of withstanding high axial forces as well as forces in the plane transverse to the bending plane, which resists transverse forces and allows for the tendon routing strategy to minimize inter joint coupling;

the elongated elastic members comprise nickel titanium alloy tubes; and the bidirectional asymmetric crenulations are micromachined with a femtosecond laser.

\* \* \* \* \*